(12) United States Patent
VanDusseldorp et al.

(10) Patent No.: US 6,673,071 B2
(45) Date of Patent: Jan. 6, 2004

(54) PARTIAL ABLATION PROCEDURE AND DEVICE THEREFOR

(76) Inventors: Gregg A. VanDusseldorp, 2177-A Green Valley Dr., Crown Point, IN (US) 46307; Arthur M. McCausland, 571 Mills Rd., Sacramento, CA (US) 94203; Vance McCausland, 3016 Waverly Dr., Los Angles, CA (US) 90001

( * ) Notice: Subject to any disclaimer, the term of this patent is extended or adjusted under 35 U.S.C. 154(b) by 0 days.

(21) Appl. No.: 10/065,014

(22) Filed: Sep. 10, 2002

(65) Prior Publication Data

US 2003/0032953 A1 Feb. 13, 2003

Related U.S. Application Data

(63) Continuation of application No. 09/792,403, filed on Feb. 23, 2001, now abandoned.
(60) Provisional application No. 60/185,172, filed on Feb. 24, 2000.

(51) Int. Cl.[7] .............................................. A61B 18/18
(52) U.S. Cl. ............................................. 606/41; 606/47
(58) Field of Search .......................... 606/41, 44, 46–52

(56) References Cited

U.S. PATENT DOCUMENTS 5,836,947 A  * 11/1998  Fleischman et al. .......... 606/47
5,938,661 A  *  8/1999  Hahnen ....................... 606/46
6,152,920 A  * 11/2000  Thompson et al. ........... 606/47
6,237,605 B1 *  5/2001  Vaska et al. .................. 606/41
6,315,778 B1 * 11/2001  Gambale et al. .............. 606/46

FOREIGN PATENT DOCUMENTS

DE            3220940    * 12/1983  .................. 606/47

* cited by examiner

*Primary Examiner*—David M. Shay
(74) *Attorney, Agent, or Firm*—Hartman & Hartman, P.C.; Gary M. Hartman; Domenica N. S. Hartman

(57) ABSTRACT

A device and procedure for performing resections and ablations, and more particularly for performing a partial ablation of the endometrium to treat uterine bleeding (menorrhagia), by which complications caused by "total" endometrial ablation or resection are avoided. The device includes a support member, a first conductor member supported with the support member and reciprocable relative to the support member, the first conductor member having an end that extends beyond the support member, a nonconducting member interconnecting the end of the first conductor member with the support member, and at least one flexible conductor member supported with the support member and interconnected with the end of the first conductor member. Retraction of the first conductor member relative to the support member causes the nonconducting member and the flexible conductor member to expand outward from the first conductor member in substantially opposite directions.

21 Claims, 3 Drawing Sheets

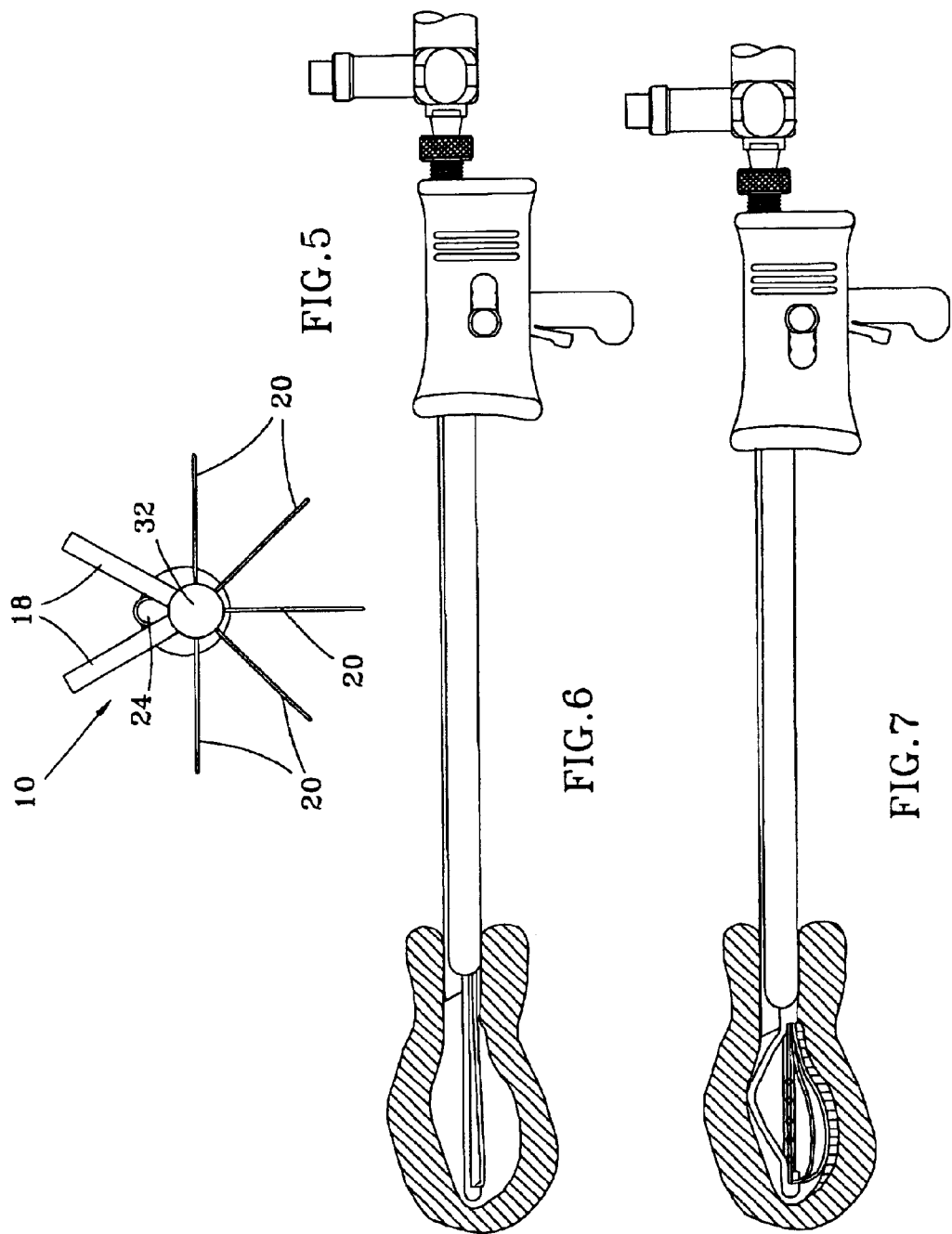

PARTIAL ABLATION PROCEDURE AND DEVICE THEREFOR

CROSS REFERENCE TO RELATED APPLICATIONS

This is a continuation-in-part patent application of U.S. patent application Ser. No. 09/792,403, filed Feb. 23, 2001 abandon, which claims the benefit of U.S. Provisional Application No. 60/185,172, filed Feb. 24, 2000.

BACKGROUND OF INVENTION

1. Field of the Invention

The present invention generally relates to procedures and equipment for performing resections and ablations, particularly of the endometrium to control uterine bleeding (menorrhagia). More particularly, this invention relates to a device and procedure for performing a partial ablation, e.g., of the endometrium, by which complications caused by total/global ablation or resection are minimized or avoided.

2. Description of the Related Art

Electrosurgical resection is a procedure in which damaged, diseased or enlarged tissue is removed with an electrocautery probe. An example is endometrial ablation, which is an electrosurgical alternative treatment to hysterectomy in women with menorrhagia (abnormal uterine bleeding). Another example of electrosurgical resection is transurethral resection of the prostate (TURP), in which prostate tissue is removed by means of an electrocautery probe (e.g., a cutting loop) that is passed through the urethra by means of a resectoscope.

In endometrial ablation, the entire endometrium is ablated to expose myometrium, hence the term total (global) endometrial ablation. Total ablation of the endometrium is currently performed by three methods: through a cystoscope or endoscope using a laser and/or laser fiber to deliver energy to the tissue; through a resectoscope using electrodes, such as the roller and cutting loop electrodes taught in U.S. Pat. Nos. 5,759,183 and 5,919,190 to VanDusseldorp in a procedure known as total rollerball endometrial ablation (TREA); and by the use of intrauterine endometrial ablation devices. Conventional ablation and resection procedures often entail the use of an electrode or laser that is inserted into a cavity (e.g., endometrial cavity) through a resectoscope or hysteroscope. The electrode or laser tip is then moved along the walls of the uterus in a pattern (such as in resection), delivering radio frequency (RF) or laser energy to the tissue. Depending on power and wave length combinations, this procedure totally resects and/or coagulates (ablates) both the anterior and posterior walls of the endometrial cavity. Other global endometrial ablation devices incorporate other technologies to heat or freeze the walls of the cavity (e.g., the endometrium), such that the wall tissue dies. Though some of these devices are placed through a resectoscope or hysteroscope, they are not necessarily in the form of a conventional "resectoscope" electrode.

Each of the above-noted modalities ablates, resects or freezes the entire intrauterine cavity, accounting for the term total or global ablation, which is represented in FIG. 1. It is believed that there are various unique long-term complications that can follow total endometrial ablation. After the endometrium is ablated (destroyed), myometrium is exposed. After the distention media is removed, the intrauterine walls collapse upon each other and may grow together, causing an intrauterine contracture which reduces the cavity into a narrow tubular structure often obstructing the corneal area. Endometrial tissue has a tendency to persist or regenerate in the corneal and intramural tubal areas, which can bleed causing symptomatic corneal hematometra (CH) or retrograde menstruation with resultant endometriosis. In patients who have had a tubal ligation, retrograde bleeding can cause a painful tubal distention known as post ablation tubal sterilization syndrome (PATSS). Central hematometra is generally caused by resecting/ablating too far into the upper cervical canal. Devices or procedures that totally or globally ablate the interior walls of the uterus increase this potential problem. Moreover, intrauterine contracture and scarring caused by total ablation may delay bleeding and the diagnosis of endometrial cancer. Nonetheless, conventional wisdom is that total endometrial ablation is required to treat menorrhagia.

SUMMARY OF INVENTION

The present invention provides a very controlled "partial" ablation treatment, and a device for performing the partial ablation treatment. According to the invention, partial ablation of the endometrium avoids the development of adhesions and contracture, which are believed to occur following total (global) endometrial ablation procedures conventionally employed to treat menorrhagia. The device of this invention is able to perform a partial ablation in a single procedure, such as by providing controlled electrosurgical ablation of either the anterior or posterior endometrial wall, instead of both as previously done with prior art devices and procedures in accordance with conventional wisdom. The device and procedure of the invention are able to correct menorrhagia without causing intrauterine scarring, with the preferred result being hypomenorrhea or eumenorrhea, not amenorrhea.

Accordingly, the partial ablation treatment of this invention is contrary to the conventional wisdom that total ablation is required to treat menorrhagia.

The partial ablation device of the invention generally includes a support member, a first conductor member supported with the support member and reciprocable relative to the support member with one end of the first conductor member extending beyond the support member, at least one electrically nonconducting member preferably interconnecting the support member and the first conductor member, and at least one flexible conductor member supported with the support member and interconnected with the first conductor member. Retraction of the first conductor member relative to the support member moves the end of the first conductor member toward the support member, causing the nonconducting and conductor members to expand outward from the first conductor member in substantially opposite directions.

When performed with the device described above, the partial ablation procedure of this invention generally entails the steps of inserting the device within the intrauterine cavity of the human body, and then retracting the first conductor member relative to the support member to move the end of the first conductor member toward the support member, causing the nonconducting and conductor members to expand outward from the first conductor member in substantially opposite directions. A current is then caused to flow through the flexible conductor member(s) so as to ablate and/or coagulate one wall (partial) of the tissue of the intrauterine cavity.

From the above, one skilled in the art will realize that the partial ablation procedure of this invention is contrary to conventional wisdom that total endometrial ablation is required to treat menorrhagia. With the device of this invention, the partial ablation procedure is relatively quick and requires less expertise than that required to operate a conventional resectoscope for prior art total (global) ablation procedures. In one embodiment of the invention, the device is adapted for use in a doctor's office or in a hospital or surgery center operating room, and has the advantage of direct vision for placement as well as observation of the ablation process. In another embodiment, the device is adapted to have a smaller diameter for use in a doctor's office as a standalone self-contained device placed under ultrasound. With the above embodiments of the invention, the entire office visit may be reduced to an hour, with only ten to fifteen minutes being potentially necessary for the actual procedure. In still another embodiment, a larger device is adapted for use in a hospital or surgery center operating room, and can be placed under direction vision or through any standard resectoscope or hysteroscope. In addition to being adapted to perform the partial ablation procedure of this invention, an advantage of each embodiment of the device is the ability to be manufactured to allow for its disposal after the procedure.

Other objects and advantages of this invention will be better appreciated from the following detailed description.

BRIEF DESCRIPTION OF DRAWINGS

FIGS. 2 through 5 show a device for performing a partial ablation procedure in accordance with a first embodiment of the invention, in which FIG. 2 is a perspective view of the entire device when in a stowed (closed) position, FIGS. 3 and 4 are perspective views of the distal end of the device when in the stowed and deployed (open) positions respectively, and FIG. 5 is an end view of the device when in the deployed position.

FIGS. 6 and 7 represent the device of FIGS. 2 through 5 placed in uterus under direct vision, in which FIG. 6 shows the device in the stowed position for insertion into the intrauterine cavity, and FIG. 7 shows the device in the deployed position and the result of partial ablation performed with the device.

DETAILED DESCRIPTION

Figure 1:
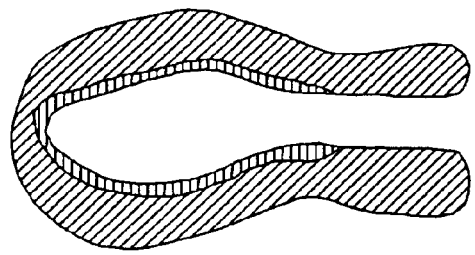
FIG. 1 represents an intrauterine cavity that has been subjected to total (global) endometrial ablation in accordance with prior art endometrial ablation procedures.

A partial ablation device 10 in accordance with a first embodiment of the invention is depicted in FIGS. 2 through 5. While the device 10 will be discussed in reference to endometrial ablation, those skilled in the art will recognize that the device can have other potential uses, such as for performing transurethral resection of the prostate (TURP).

The partial ablation device 10 is represented as including a sheath 12 mounted to any suitable handle 22, to which a conventional pediatric telescope 26 is shown mounted. The device 10 is provided with a channel 24 to accept the telescope 26, so that the device 10 can be placed and the procedure performed under direct vision. Materials known and used for prior art ablation devices can be used to fabricate the sheath 12, handle 22 and channel 24 of the device 10.

A central conductor 14 is disposed within the sheath 12 so that one end (distal end) of the central conductor 14 extends outside the sheath 12. The central conductor 14 is capable of reciprocal movement within the sheath 12 through the operation of an actuation lever 28, to be further discussed below. The central conductor 14 preferably has an internal flow channel with a row of outlet ports 16 along its length (visible with the embodiment of FIG. 8) to enable an irrigation fluid to be used. The handle 22 is represented as having a fluid inlet or stopcock 30 through which an irrigation fluid can be introduced into the flow channel of the central conductor 14. In addition to irrigation fluids, a gas such as carbon dioxide can be introduced through the flow channel for purposes of cavity insuflation during the partial endometrial ablation procedure of this invention. Suitable materials for the central conductor 14 include AISI type 304 stainless steel, as used to form hypodermic tubing, though it is foreseeable that other materials could be used.

The partial ablation device 10 is further represented as having flexible electrically-conductive wires 20 and a pair of flexible nonconducting members 18. The conductive wires 20 extend from the sheath 12 and are connected to the distal end of the central conductor 14. While shown as being formed of round wire, other cross-sections are possible, including rectangular. Suitable materials for the wires 20 include tungsten and stainless steels, though it is foreseeable that other materials could be used. The nonconducting members 18 interconnect the end of the central conductor 14 with the sheath 12. For this purpose, the central conductor 14 is shown as having a cap 32 on its distal end, with the nonconducting members 18 shown as being formed integral with the cap 32 and sheath 12. Accordingly, suitable materials for the nonconducting members 18 and cap 32 are those suitable for the sheath 12. The length over which the nonconductive members 18 and wires 20 extend along the central conductor 14 can vary, with lengths between about four to about seven centimeters believed to be particularly suitable for partial endometrial ablation. While two nonconducting members 18 are shown in FIGS. 2 through 5 as being angularly spaced about 80 degrees apart, it is foreseeable that various numbers and spacing of the members 18 could be used.

In describing the nonconducting members 18, the term "nonconducting" is defined herein as meaning a dielectric, such that a current applied to the central conductor 14 will not flow at any significant level when a RF electrosurgical current is applied by a conventional electrosurgical generator. Furthermore, the term "flexible" is meant to convey that the nonconducting members 18 are able to flex in the manner shown in FIGS. 4 and 5, or the functional equivalent, and does not require that the nonconducting members 18 are formed of a flexible material. All that is required is that the nonconducting members 18 are capable of being flexed outward from the central conductor 14, requiring the ability to bend at or near the intersection of the conducting members 18 with the cap 32, bend at some point away from the cap 32 (e.g., the intersection of the conducting members 18 with the sheath 12), and bend or flex continuously or at location(s) of the conducting members 18 therebetween.

Figure 2:
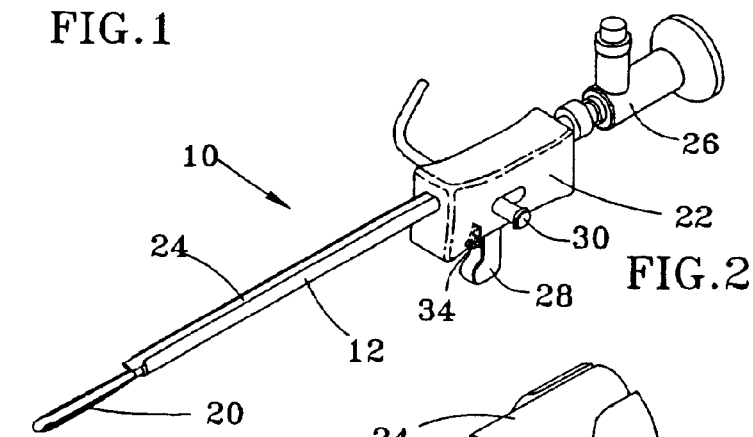
Figure 3:
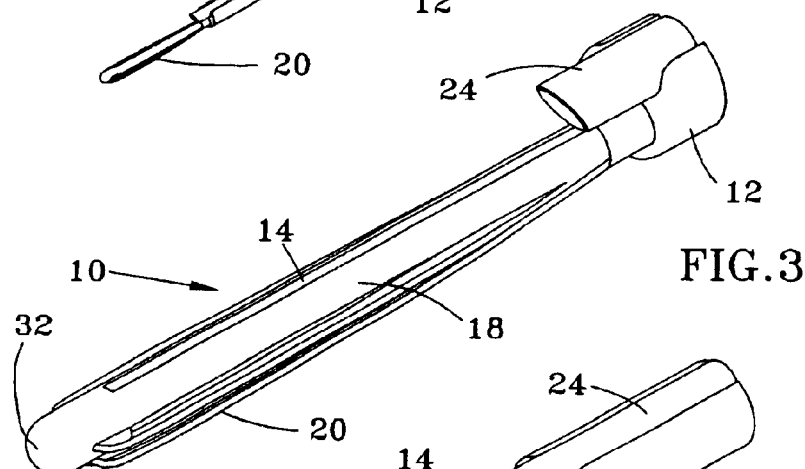
Figure 4:
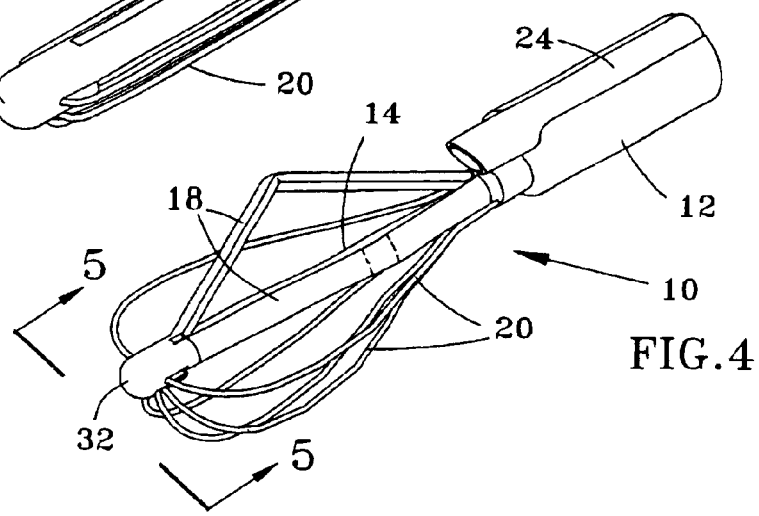

In comparing FIGS. 3 and 4, one can see that the device has a stowed position in which the nonconducting members 18 and the wires 20 are substantially parallel to the central conductor 14, and that retracting the central conductor 14 into the sheath 12 causes the cap 32 (and the distal end of the central conductor 14) to move toward the sheath 12, causing the nonconducting members 18 and the wires 20 to be elastically displaced (expand) radially outward away from the central conductor 14 in substantially opposite directions, substantially along their entire lengths. As a result, the nonconducting members 18 are able to be pressed into contact with the cavity wall opposite the cavity wall to be treated, causing the conductive wires 20 to be pressed into contact with the cavity wall intended for the partial ablation procedure of this invention. FIGS. 6 and 7 represent the partial endometrial ablation procedure of this invention, in which FIG. 6 shows the device 10 as having been placed in the intrauterine cavity under direct vision while in the stowed (closed) position (FIGS. 2 and 3). Once placed, the device 10 is deployed as shown in FIG. 7 (and FIGS. 4 and 5) to perform the partial ablation procedure. As represented in FIG. 7, partial endometrial ablation has been performed on the posterior endometrium and adjacent myometrium. During the procedure, RF electrosurgical current, which can be generated by a conventional electrosurgical generator (not shown), is conducted through the wires 20 (and central conductor 14). As previously noted, deployment occurs through operating the actuation lever 28. In a preferred embodiment, the actuation lever 28 is operable as a ratchet, so that the device 10 can be opened to any one of a number of different deployed positions, each characterized by the nonconducting members 18 and conductive wires 20 being flexed to attain a predeterminable diameter. As such, the device 10 can be opened to a desired diameter depending on the size of the intrauterine cavity. A release 34 is provided to allow the ratchet to be released and the device 10 collapsed to return to the stowed position of FIGS. 2, 3 and 6.

As represented in FIG. 7, the partial endometrial ablation procedure of this invention is contrary to the conventional wisdom of using total endometrial ablation procedures to treat menorrhagia. Instead of both the anterior and posterior endometrium being ablated, as depicted in FIG. 1, only the anterior or posterior endometrium is ablated. According to the invention, performing ablation on only one of the intrauterine cavity walls avoids the exposure of myometrium on both intrauterine cavity walls, which is believed to allow the intrauterine walls to collapse and grow together causing intrauterine contracture. Other complications that are believed to result from total endometrial ablation and avoided with the present invention include symptomatic corneal hematometra (CH) or retrograde menstruation with resultant endometriosis, post ablation tubal sterilization syndrome (PATSS), central hematometra. advantages, particularly over prior art total ablation devices. First, the device 10 simplifies the partial ablation procedure of this invention, in which only selected regions of the intrauterine cavity are ablated. Because the device 10 is adapted to accept a telescope, the device 10 can be placed and the procedure performed under direct vision of the selected regions of the intrauterine cavity. Furthermore, a doctor can purchase the device 10 direct, and there is no additional or specialty equipment required—most gynecologists have everything they need to use the device 10 already in their offices. In addition, the device 10 provides a very effective treatment without requiring a hospital stay. Depending on the diameter of the device 10, minimal anesthesia is required to perform the partial ablation procedure, as there is less discomfort than with conventional resectoscopes that use electrodes. For example, the outer diameter of the device 10 (defined by the central conductor 14, nonconducting members 18 and conductive wires 20) when collapsed can be on the order of about six millimeters, significantly reducing discomfort to the patient. On the other hand, an outer diameter on the order of about 8.7 millimeters may be preferred, in which case the device 10 would be more suited for use in hospitals, or conducive to use by surgeons who do not have a private practice or who simply prefer that the procedure be performed in a hospital. Such a device 10 may also be beneficial for use with patients that have other health problems that would require or encourage the partial ablation procedure to be performed in a hospital.

Figure 8:
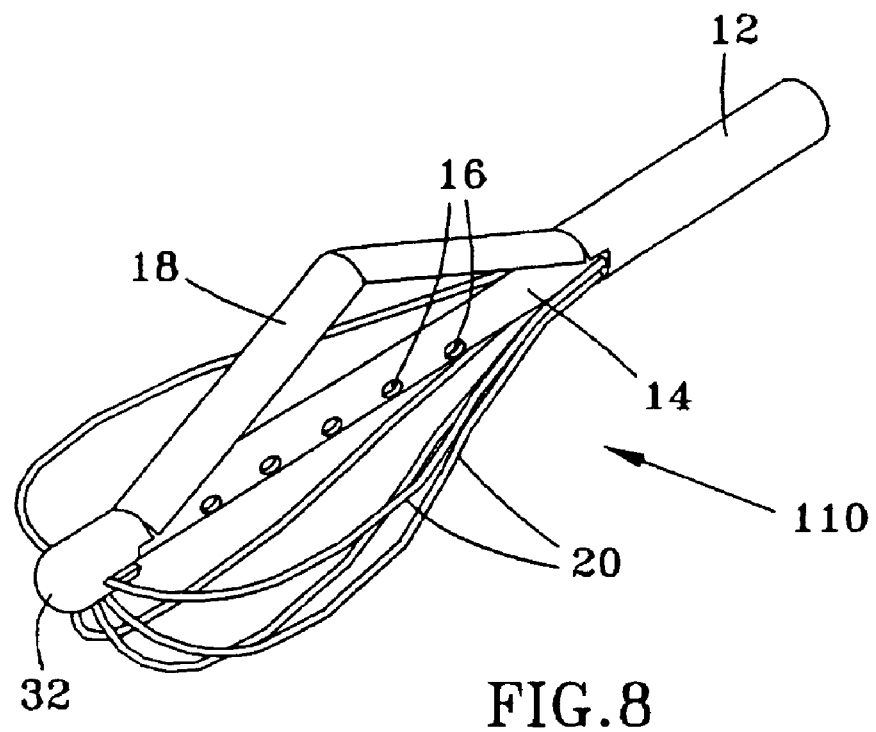
FIGS. 8 and 9 show partial ablation devices in accordance with second and third embodiments of the invention.

FIG. 8 represents a device 110 in accordance with a second embodiment of the invention. In this embodiment, the channel 24 is omitted, requiring that the device 110 is placed (blind) via ultrasound. The device 110 is also depicted as having a single nonconducting member 18. The device 110 can be manufactured to have an outer diameter (defined by the central conductor 14, nonconducting member 18 and conductive wires 20) on the order of about four millimeters, and is therefore particularly practical for use in a doctor's office because usually no cervical dilation would be required.

Figure 9:
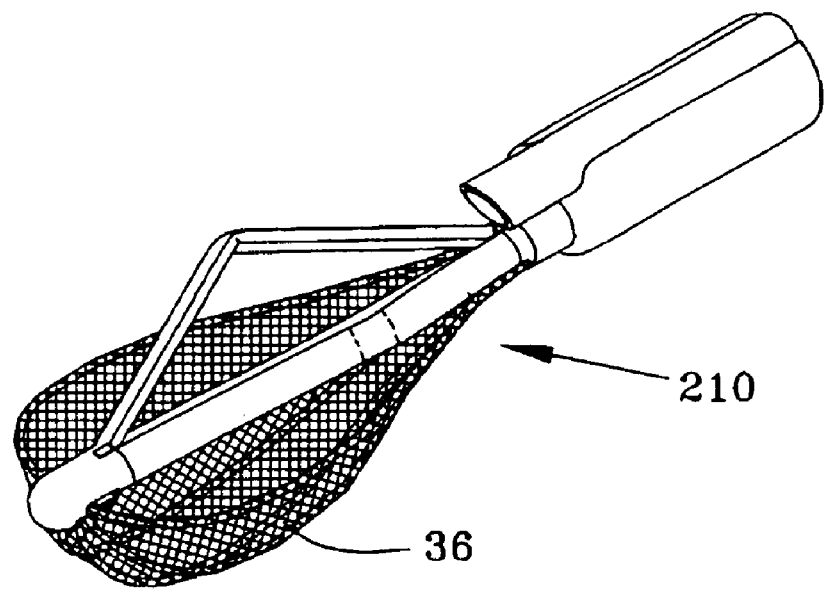

FIG. 9 represents a device 210 in accordance with a third embodiment of the invention, in which the wires 20 support a conductive material 36, such as a metal foil, wire mesh, or resilient plastic with a conductive film deposited or otherwise carried thereon. The conductive material 36 allows for a more uniform distribution of the RF energy applied through the wires 20. Also within the scope of the invention are various other modifications, such as those that would allow the use of the devices 10 and 110 in combination with a resectoscope or hysteroscope. In addition, the nonconducting members 18 may be formed to have memory, and mounted with the central conductor 14 and the conductive wires 20 within a second sheath (not shown) so that the nonconducting members 18 are biased for deflection outward away from the central conductor 14 when extended outside of the second sheath. Such an embodiment could be used to perform a partial ablation after resection of endometrial polyps or submucous fibroid. For use in combination with a resectoscope or hysteroscope, another alternative embodiment of the device 10 is to omit the nonconducting members 18, relying solely on visual observation to perform the partial ablation procedure of this invention.

While the invention has been described and illustrated in terms of specific embodiments, it is apparent that other forms could be adopted by one skilled in the art. For example, the devices could differ in appearance and construction from the embodiments shown in the Figures, and appropriate materials could be substituted for those noted. Furthermore, while adapted to perform partial ablation, the devices shown in the Figures could be used to perform a total ablation, in which case the device would be turned over to ablate the wall opposite the one ablated in the first procedure. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention. Instead, the scope of the invention is to be limited only by the following claims.

What is claimed is:

1. A partial ablation device comprising:
    a support member;
    a first conductor member supported with the support member and reciprocable relative to the support member, the first conductor member having an end that extends beyond the support member;
    at least one nonconducting member interconnecting the first conductor member with the support member; and
    at least one flexible conductor member supported with the support member, extending along the first conductor member, and interconnected with the first conductor member;

wherein the device has a stowed position in which the first conductor member is extended from the support member and the nonconducting member and the flexible conductor member are disposed alongside the first conductor member;

wherein the support member, the first conductor member, the nonconducting member and the flexible conductor member are interconnected so that retraction of the first conductor member relative to the support member causes the end of the first conductor member to move toward the support member and causes the nonconducting member and the flexible conductor member to expand outward and away from the first conductor member and away from each other; and wherein, when the first conductor member is retracted to expand the nonconducting member and the flexible conductor member the flexible conductor member is operative to perform ablation of a first wall region of a cavity of the human body while a second wall region of the cavity is held apart from the first wall region by the nonconducting member so that the second wall region does not undergo ablation.

2. A partial ablation device according to claim 1, wherein the device comprises two of the nonconducting members.

3. A partial ablation device according to claim 1, wherein the first conductor member has an internal channel therein and at least one outlet port fluidically connected thereto, the internal channel and the at least one outlet port being operative to cause a fluid flowing through the internal channel to be discharged from the first conductor member through the at least one outlet port.

4. A partial ablation device according to claim 1, further comprising a channel disposed along the support member, the channel being sized to receive a telescope therein.

5. A partial ablation device according to claim 1, further comprising a cap on the end of the first conductor member, the nonconducting member interconnecting the cap and the support member.

6. A partial ablation device according to claim 5, wherein the cap is nonconducting.

7. A partial ablation device according to claim 1, wherein the device is in a deployed position and the nonconducting member and the flexible conductor member are elastically displaced radially outward along substantially their entire lengths when the first conductor member is retracted relative to the support member.

8. A partial ablation device according to claim 7, wherein the device further comprises ratchet means for retracting the first conductor member relative to the support member, wherein the device has a plurality of deployed positions.

9. A partial ablation device according to claim 1, wherein the device comprises a plurality of flexible conductor members, the device further comprising an electrically-conductive material supported by and between the flexible conductor members.

10. A partial ablation device according to claim 9, wherein the electrically-conductive material is chosen from the group consisting of metal foil, wire mesh, and resilient plastic with a conductive film deposited or otherwise carried thereon.

11. A partial endometrial ablation device comprising:
an elongate support member;
an elongate first conductor member reciprocably supported within the support member for reciprocating movement relative thereto in oppositely-disposed first and second directions, the first conductor member having an end that extends outside the support member;
at least one flexible nonconducting member having a first end interconnected with the support member and having a second end interconnected with the end of the first conductor member; and a plurality of flexible conductor members, each having a first end interconnected with the support member and having a second end electrically interconnected with the end of the first conductor member for conducting a current through the first and flexible conductor members;

wherein the support member, the first conductor member, the flexible nonconducting member and the flexible conductor members are interconnected so that extension of the first conductor member in the first direction relative to the support member causes the end of the first conductor member to move away from the support member and establishes a stowed position in which the flexible nonconducting member and the flexible conductor members are substantially parallel to and alongside the first conductor member and wherein retraction of the first conductor member in the second direction relative to the support member causes the end of the first conductor member to move toward the support member and establishes a deployed position in which the flexible nonconducting member and the flexible conductor members are expanded outward and away from the first conductor member and in substantially opposite directions to each other; and wherein, when the first conductor member is retracted to expand the flexible nonconducting member and the flexible conductor members the flexible conductor members are operative to perform ablation of a first wall region of an intrauterine cavity of the human body while an oppositely-disposed second wall region of the intrauterine cavity is held apart from the first wall region by the flexible nonconducting member so that the second wall region does not undergo ablation.

12. A partial ablation device according to claim 11, further comprising a nonconducting cap on the end of the first conductor member, the flexible nonconducting member interconnecting the cap and the support member.

13. A partial ablation device according to claim 11, wherein the device comprises two of the flexible nonconducting members.

14. A partial ablation device according to claim 11, wherein the device further comprises ratchet means for retracting the first conductor member relative to the support member such that the device has a plurality of deployed positions.

15. A partial ablation device according to claim 11, further comprising a channel disposed along the support member the channel being sized to receive a telescope therein.

16. A partial ablation device according to claim 11, the device further comprising an electrically-conductive material supported by and between the flexible conductor members the electrically-conductive material being chosen from the group consisting of metal foil, wire mesh, and resilient plastic with a conductive film deposited or otherwise carried thereon.

17. A partial endometrial ablation procedure to treat menorrhagia, the procedure comprising the steps of
inserting a partial ablation device within the intrauterine cavity of the human body; and then
causing a current to flow through at least one flexible conductor of the ablation device to cut and/or coagulate tissue of a first wall region of the intrauterine cavity while an oppositely-disposed second wall region of the intrauterine cavity is held apart from the first wall region by at least one nonconducting member.

18. A partial endometrial ablation procedure according to claim 17, wherein the partial ablation device comprises a first conductor member, the at least one nonconducting member and the at least one flexible conductor member that are substantially parallel to each other when the partial ablation device is inserted into the intrauterine cavity, the procedure further comprising the step of expanding the nonconducting member and the flexible conductor member outward from the first conductor member in substantially opposite directions, the nonconducting member contracting one of the anterior or posterior walls of the intrauterine cavity the flexible conductor member contacting the other of the anterior or posterior walls of the intrauterine cavity, the current flowing through the flexible conductor member to cut and/or coagulate tissue on the other of the anterior or posterior walls of the intrauterine cavity.

19. A partial endometrial ablation procedure according to claim 17, wherein the partial ablation device comprises a support member, a first conductor member supported with the support member and reciprocable relative to the support member, the first conductor member having an end that extends beyond the support member, the at least one nonconducting member interconnecting the end of the first conductor member with the support member and the at least one flexible conductor member supported with the support member and interconnected with the end of the first conductor member, and wherein following the insertion step the first conductor member is retracted relative to the support member to move the end of the first conductor member toward the support member, causing the nonconducting member and the at least one flexible conductor member to expand outward from the first conductor member in substantially opposite directions, the nonconducting member contacting one of the anterior or posterior walls of the intrauterine cavity, the flexible conductor member contacting the other of the anterior or posterior walls of the intrauterine cavity, the current flowing through the flexible conductor member to cut and/or coagulate tissue on the other of the anterior or posterior walls of the intrauterine cavity.

20. A partial endometrial ablation procedure comprising the steps of:
    inserting an ablation device within the intrauterine cavity of the human body; and then
    causing a current to flow through at least one conductor member of the ablation device to perform a controlled and selective electrosurgical ablation of a first wall region of the intrauterine cavity and not a second wall region of the intrauterine cavity by holding the second wall region apart from the first wall region with at least a second member through which current does not flow.

21. A partial endometrial ablation procedure according to claim 20, wherein the ablation device is a partial ablation device comprising a first conductor member, the second member and the at least one conductor member, the procedure further comprising the step of expanding the second member and the at least one conductor member outward from the first conductor member in substantially opposite directions, the second member contacting the second wall region of the intrauterine cavity, the at least one conductor member contacting the first wall region of the intrauterine cavity, the current flowing through the at least one conductor member to cut and/or coagulate tissue of the first wall region of the intrauterine cavity.

* * * * *